(12) United States Patent
Basiony (10) Patent No.: US 11,173,321 B2
(45) Date of Patent: Nov. 16, 2021

(54) SYSTEM FOR ITS USE TO TREAT LEUKEMIA

(71) Applicant: Mohamed A Basiony, Kenmore, WA (US)

(72) Inventor: Mohamed A Basiony, Kenmore, WA (US)

( * ) Notice: Subject to any disclaimer, the term of this patent is extended or adjusted under 35 U.S.C. 154(b) by 216 days.

(21) Appl. No.: 16/675,862

(22) Filed: Nov. 6, 2019

(65) Prior Publication Data

US 2020/0147409 A1    May 14, 2020

Related U.S. Application Data

(60) Provisional application No. 62/758,557, filed on Nov. 10, 2018.

(51) Int. Cl.
*A61N 5/06* (2006.01)
*A61M 1/30* (2006.01)
(Continued)

(52) U.S. Cl.
CPC .......... *A61N 5/0624* (2013.01); *A61L 2/0047* (2013.01); *A61M 1/30* (2013.01); *A61M 1/34* (2013.01); *A61M 1/3681* (2013.01); *A61N 5/0601* (2013.01); *A61M 1/0259* (2013.01); *A61M 2202/0413* (2013.01); *A61M 2202/203* (2013.01); *A61M 2205/053* (2013.01);
(Continued)

(58) Field of Classification Search
CPC .. A61B 5/0538; A61L 2/0047; A61M 1/0259; A61M 1/30; A61M 1/34; A61M 1/3681; A61M 2202/0413; A61M 2202/203; A61M 2205/053; A61N 2005/0602; A61N 2005/0661; A61N 5/0601; A61N 5/0624; A61N 5/06–2005/073
See application file for complete search history.

(56) References Cited

U.S. PATENT DOCUMENTS 9,492,574 B2 * 11/2016 Rasooly .............. A61M 1/1696
2006/0217789 A1 * 9/2006 Perez .................. A61N 5/0616
607/94

(Continued)

OTHER PUBLICATIONS

Berger, M., Niebuhr, D., Allers, M., & Zimmermann, S. (2018). P1DH. 14-Continuous Non-Invasive Sodium Monitoring in Extracorporeal Circuits. Proceedings IMCS 2018, 683-684. doi: 10.5162/IMCS2018/P1DH.14 Published Jul. 15, 2018 (Year: 2018).*

(Continued)

*Primary Examiner* — Jonathan T Kuo (57) ABSTRACT

A system to be used to treat Leukemia, comprises a device to power, control and monitor an ultraviolet radiation as well as to monitor a blood contactless conductivity; and a catheter assembly with an inner dialysis catheter, an ultraviolet radiation source and a differential coil sensor. The system is using wavelengths of ultraviolet radiation to destroy infectious microbes that are in the blood and that are inside circulating tumor cells directly and indirectly as well as to destroy infectious microbes at primary tumor location (bone marrow). This is done without withdrawing the blood out of the body. Furthermore, the system measures a blood conductivity to evaluate the treatment process in a real time during the operation.

3 Claims, 7 Drawing Sheets

(51) Int. Cl.
*A61L 2/00* (2006.01)
*A61M 1/34* (2006.01)
*A61M 1/36* (2006.01)
*A61M 1/02* (2006.01)

(52) U.S. Cl.
CPC ............... *A61N 2005/0602* (2013.01); *A61N 2005/0661* (2013.01)

(56) References Cited

U.S. PATENT DOCUMENTS

| | | | | |
|---|---|---|---|---|
| 2014/0334974 | A1* | 11/2014 | Rasooly | A61L 2/10 422/24 |
| 2015/0283318 | A1* | 10/2015 | Wang | A61B 18/20 210/638 |
| 2016/0008624 | A1* | 1/2016 | Grossman | A61N 5/0624 607/89 |
| 2017/0182305 | A1* | 6/2017 | Kermode | A61M 39/18 |

OTHER PUBLICATIONS

M. Berger, F. Sellering, H. Röhrich, H. Mansour, T. Perl and S. Zimmermann, "A Differential Transformer for Noninvasive Continuous Sodium Monitoring During Dialysis Treatment," 2019 IEEE Sensors, 2019, pp. 1-4, doi: 10.1109/SENSORS43011.2019. 8956610. Published Oct. 30, 2019 (Year: 2019).*

Berger, Marc, et al. "Contactless and continuous sodium concentration monitoring during continuous renal replacement therapy." Sensors and Actuators B: Chemical 320 (2020): 128372. https://doi.org/10.1016/j.snb.2020.128372 Published Oct. 1, 2020 (Year: 2020).*

* cited by examiner

SYSTEM FOR ITS USE TO TREAT LEUKEMIA

BACKGROUND

Leukemia is a disorder involving blood cells. Healthy cells form in the bone marrow and mature into red blood cells, white blood cells and platelets. In patients with leukemia, these cells do not mature as they should be or they transform into irregular blood cells that do not function normally.

Infections may be one of Leukemia causing factors. Globally, almost 20% of cancers are related to infection agents (Damania, B.: DNA tumor viruses and human cancer. Trends Microbiol., 2006; 15: 38-44). Oncogenic viruses (tumor viruses) promote cell transformation, prompt uncontrollable cell generation, and lead to the development of malignant tumors (Cupić, M., Lazarević, I., Kuljić-Kapulica, N.: Oncogenic viruses and their role in tumor formation. Srp. Arh. Celok. Lek., 2005; 133: 384-387 (article in Serbian with an abstract in English). Oncogenic abnormalities are seen in pediatric leukemias, lymphomas, and various solid tumors (Vats, T. S., Emami, A.: Oncogenes: present status. Indian J. Pediatr., 1993; 60: 193-201).

In scientific publications Virginia Livingston-Wheeler and her colleagues showed that the cancer microbe could appear as a bacterium, a virus, a fungus or a yeast—but in actuality they were all growth forms of the same germ. The microbe was found in the blood of normal and healthy people, but in the blood of terminal cancer patients the microbes were greatly increased in number. In Livingston's view, the destruction of red blood cells by cancer microbes cause the anemia that always accompanies the end stage of cancer.

Professor Mel Greaves from Institute of Cancer Research, London, in his landmark paper published in Nature Reviews Cancer Today, May 21, 2018 after 30 years of research, He reveals "likely cause of most cases of childhood leukemia as he presented strong evidence for a "delayed infection" theory for the cause of all, in which early infection is beneficial to prime the immune system but later infection in the absence of earlier priming can trigger leukemia".

Based on a "delayed infection" theory, microbial exposure may lead to infection, which can lead to long-term, frequently asymptomatic carriage of the microbe with subsequent host responses, progression to premalignant lesions, and finally, to cancer. So, many microbes, including viruses, bacteria and helminths, may have been implicated in the causation of cancers and many more may be discovered.

There is a need for a system to be clinically effective in destroying infectious microbes that may be in a blood itself and may be inside circulating tumor cells in the blood directly and indirectly and also to destroy infectious microbes at primary tumor location (bone marrow that may be the initial point of infection). This may be done without withdrawing a blood out of the body to avoid more complications and infections. Furthermore, there is a need for a system that may have the ability to evaluate the treatment process in real time during the operation.

SUMMARY

Accordingly, a system comprises: a device to may power, control and monitor an ultraviolet radiation as well as to may monitor a blood contactless conductivity; and a catheter assembly with an inner dialysis catheter, an ultraviolet radiation source and a differential coil sensor is described to may address the above issues.

In operation a catheter assembly with an inner dialysis catheter, an ultraviolet radiation source and a differential coil sensor may be inserted in a femoral vein using a standard insertion technique and may be connected to the device to may irradiate a blood with an ultraviolet radiation to may destroy infectious microbes and to may measure a blood contactless conductivity during the operation.

BRIEF DESCRIPTION OF THE DRAWINGS

The accompanying drawings, which are incorporated in, and constitute a part of the specification, illustrate or exemplify embodiment of the present implementation and, together with the description, generally explain the principles and features of the present implementation. The drawings are briefly described as follows.

DETAILED DESCRIPTION

The following detailed description illustrates the principal of the disclosure by way of example not by way of limitation. While a reference use of the present disclosure describes a system to be used to treat leukemia, as those of ordinary skill in the art will readily understand. Also, it will be understood that the system may also be used to kill microbes induced cancer, and for other types of treatments, the scope of the implementation is not to be limited by the field to which the implementation is applied.

Ultraviolet blood irradiation has been used in the United States since 1927 for successful extracorporeal treatment of microbial infections in the blood. As using specific wavelengths of ultraviolet radiation in a wavelength range from about 230 to 280 nm and preferably from 248 to 270 nm to may destroy infectious microbes responsible for the infections by extensively damaging their DNA and may scramble their genetic code so they cannot reproduce, which may render them sterile and effectively dead.

Also, rayed blood may emit secondary radiations, in U.S. Pat. No. 1,683,877 filed on Mar. 3, 1927 to L. A. Edblom et al there is mentioned that "clinically experiments have further determined that beneficial energy is stored up in the rayed blood temporarily, and if such blood can be returned to the blood stream immediately after it has been rayed, it will throw off secondary radiations which will stimulate and energies the patients". This was mentioned without any further explanation. It must be pointed out that in this mentioned prior art, an ultraviolet radiation was used with an extracorporeal blood.

The secondary radiations may be as hemoglobin, meaning red blood cells, vibrate when they exposed to ultraviolet radiation. It may be due to a porphyrin molecule within hemoglobin that has an iron at its center, that may be vibrating. Hemoglobin may continuous to vibrate (for a certain period of time depending on several factors such as an ultraviolet intensity and an exposure time) and it may emit ultraviolet radiations, so it may act as a secondary ultraviolet radiations source inside the body. A time of vibration may take few hours or a day.

Each red blood cell may contain millions of hemoglobin, so the intensity of secondary radiations may be enough to may destroy microbes in the blood, to may destroy microbes inside circulating tumor cells in the blood and to may destroy microbes at an initial point of infection. Destroying microbes at an initial point of infection may represent the indirect way (away from the original source of ultraviolet) of killing microbes. Furthermore, secondary ultraviolet radiations may transmit energy to the blood that empowers a strong biochemical response thereto, increasing stabilization of white blood cells, and increasing cell membrane permeability (which may enhance the body's ability to produce antibodies).

Ultraviolet radiation may be able to destroy microbes without effecting the cells themselves as microbes may be vastly smaller than cells and they may have light sensitive amino acids, these may make them vulnerable to secondary ultraviolet radiations.

Referring again to U.S. Pat. No. 1,683,877 filed on Mar. 3, 1927 to L. A. Edblom et al there is mentioned that "Happily, observation has proven, there is a wide gap between the time of chemical destruction of foreign bacteria (chemical action of the ultraviolet rays) and impaired or physical break-down of normal cells due to over stimulation, somewhat in the relation of five seconds to two hundred and forty-five seconds". This may mean that an ultraviolet radiation may destroy microbes directly in a blood stream and indirectly (secondary radiations) at an initial point of infection without effecting the cells themselves. Destruction of microbes inside the cells by an ultraviolet radiation, may revert them into normal cells.

Figure 1:
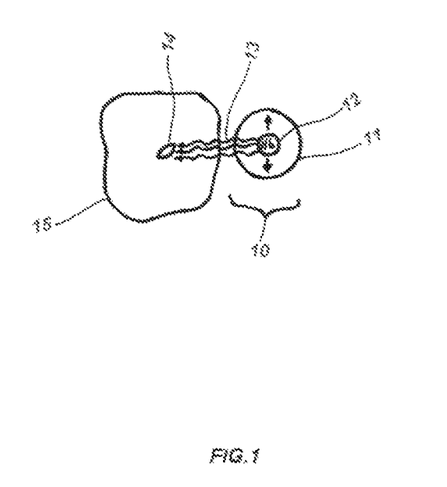
FIG. 1 illustrates hemoglobin continuous vibration after it has been rayed with an ultraviolet radiation according to the present disclosure.

Now referring to FIG. 1, it illustrates hemoglobin continuous vibration after it has been rayed with an ultraviolet radiation to destroy a microbe inside a cell (a cell in blood and a cell at an initial point of infection in bone marrow), wherein hemoglobin 12 inside a red blood cell 11 of a blood capillary 10 may continuously vibrate and may emit secondary ultraviolet radiations 13 to may destroy a microbe 14 inside a cell 15.

Figure 2:
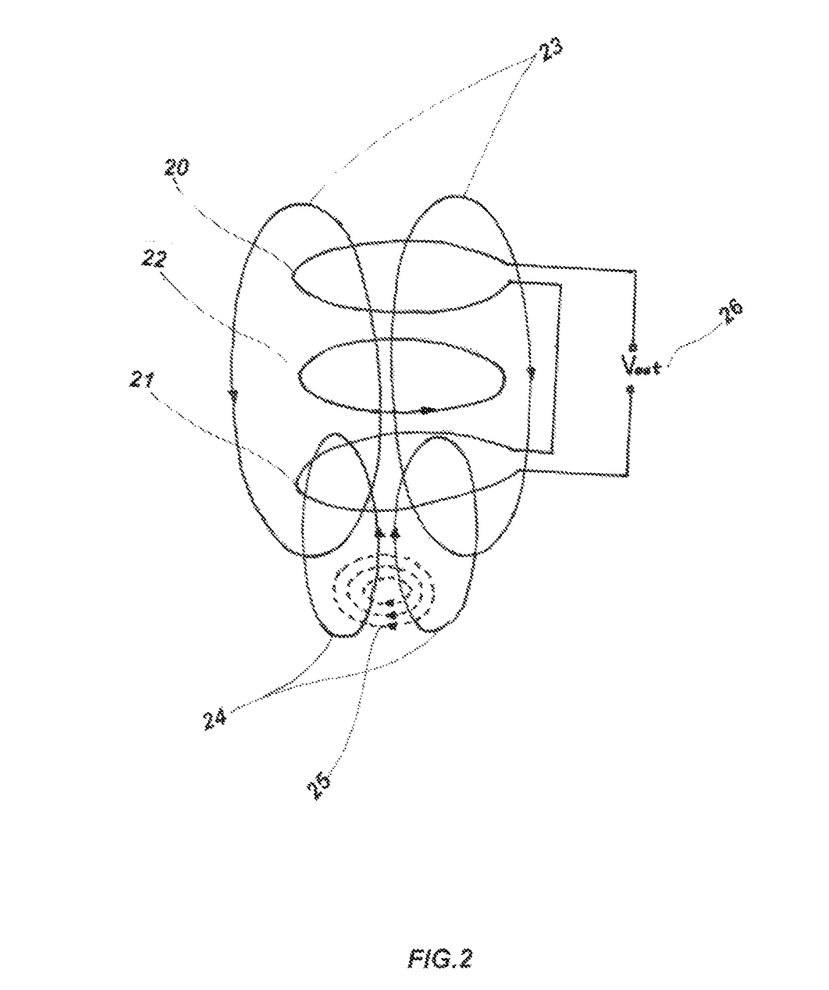
FIG. 2 illustrates a schematic representation of a differential coil sensor to measure contactless conductivity by sensing magnetic fields of induced eddy currents according to the present disclosure.

FIG. 2 illustrate a differential coil sensor to measure a blood conductivity by sensing magnetic fields of induced eddy current, wherein a transmitter coil 22 generates a primary flux 23 that induces eddy currents 25 in the blood. Primary flux 23 that is linked through two identical receiver coils 20 and 21, is equal since both receiver coils 20 and 21 are at a same distance from a transmitter coil 22 which is the source of a primary flux 23.

However, a secondary flux 24 that is generated by eddy currents 25 is linked through differentially connected receiver coils 20 and 21 unequally or in an unbalanced fashion due to the fact that a flux strength is diminished with distance. This caused a gradient voltage 26 in receiver coils 20 and 21 due to a blood conductivity. This gradient voltage 26 is directly proportional to a conductivity of a blood and it may act as measure for a contactless conductivity of a blood.

Figure 3:
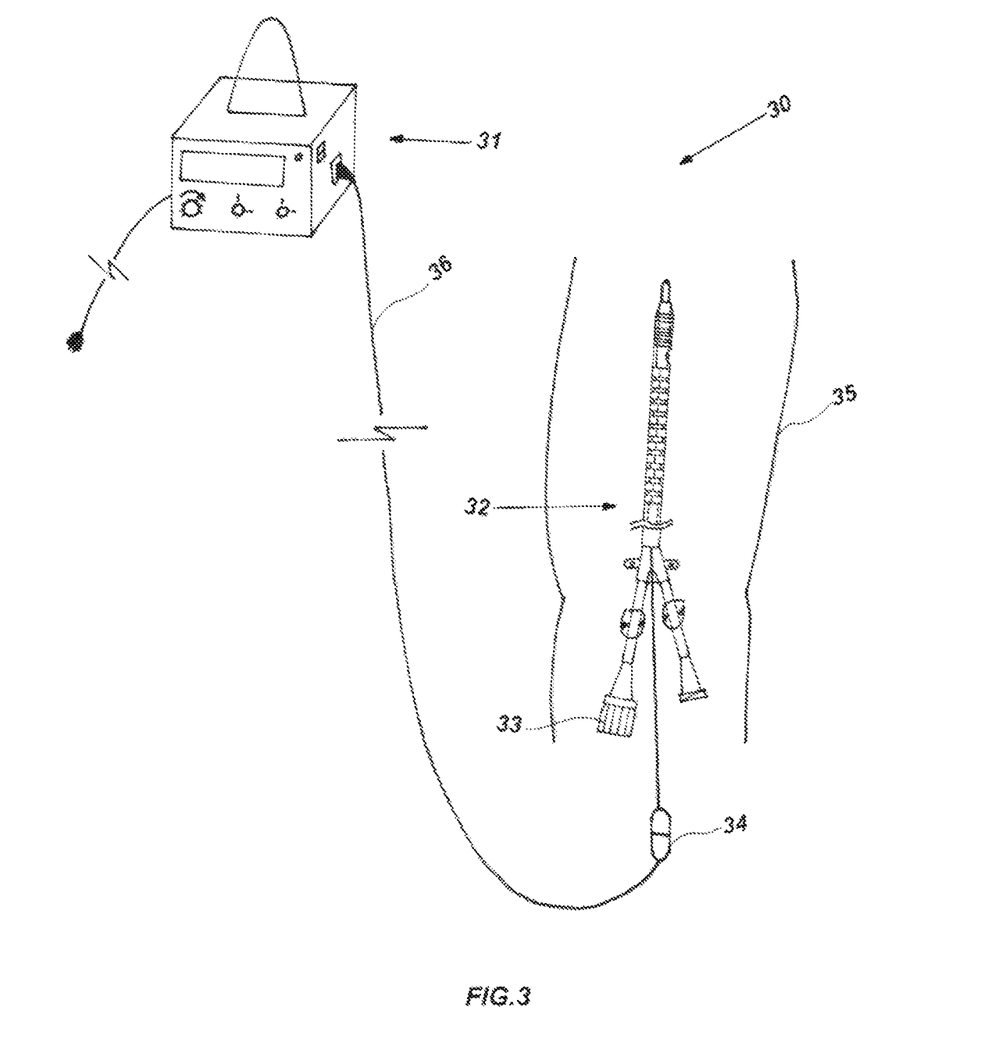
FIG. 3 illustrates a perspective view of the system comprises the device that power, control and monitor an ultraviolet radiation as well as to monitor a blood contactless conductivity and a catheter assembly according to the present disclosure.

FIG. 3 illustrate a system 30 that comprises a device 31 to may power, control and monitor an ultraviolet radiation as well as to may monitor a blood contactless conductivity; and a catheter assembly 32 with a stylet 33 for an easy insertion. A catheter assembly may be inserted in a femoral vein (not shown for simplicity) of a patient's leg 35 using a standard insertion technique and may be connected to a device 31 via a cable 36 with a socket 34. In another implementation, a catheter assembly, may be inserted in Jugular or subclavian veins. Stylet 33 may be a metal or hard plastic stylet for an easy insertion.

Figures 4, 4A:
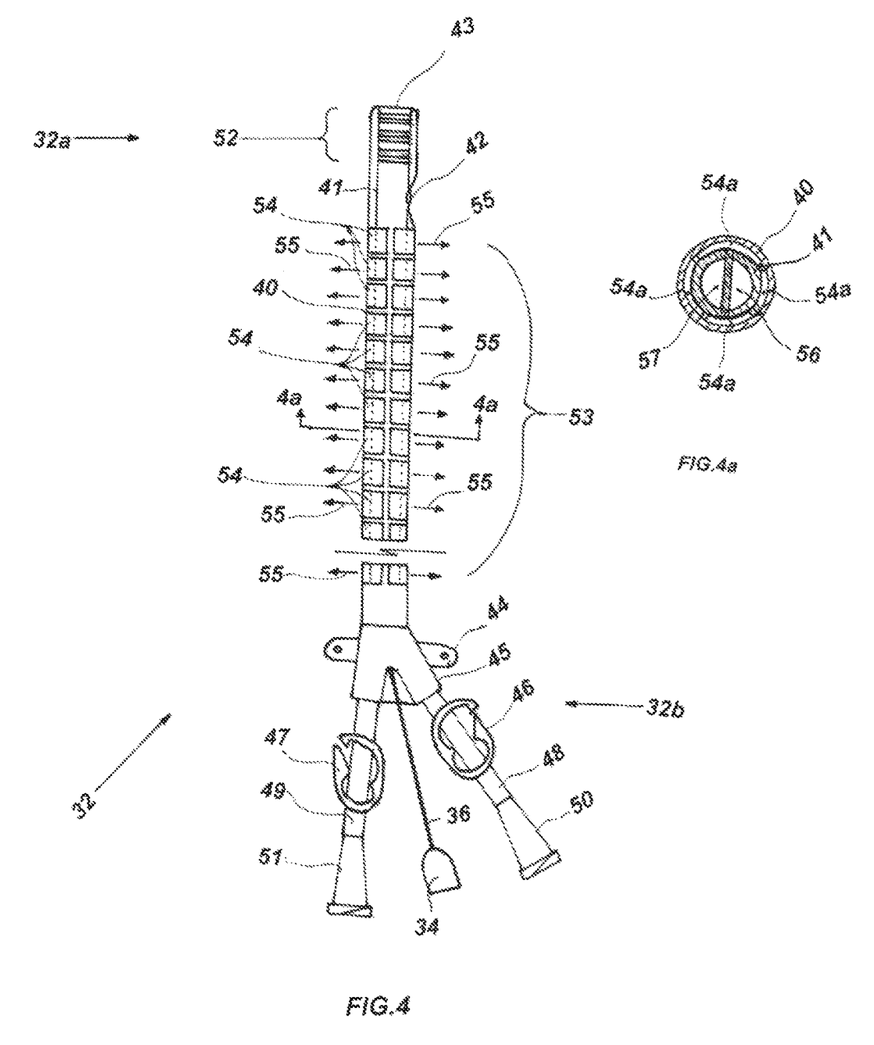
FIG. 4 is an enlarged view of the catheter assembly with an inner dialysis catheter, an ultraviolet radiation source and a differential coil sensor according to the present disclosure.
FIG. 4a is an enlarged cross-sectional view of the catheter assembly taken along line 4a-4a of FIG. 4 according to the present disclosure.

FIG. 4 illustrates an enlarged perspective view of a catheter assembly 32 without stylet 33, with an inner dialysis catheter 41, located on its outer surface a differential coil sensor 52 for a contactless conductivity measurement and an ultraviolet radiation source 53 to may irradiate a blood. Both a differential coil sensor 52 and an ultraviolet radiation source 53 are covered by a transparent outer tube 40 that it may be sealed to an outer surface of an inner dialysis catheter by adhesive, thermal or any other suitable means. The internal wires for a differential coil sensor 52 and an ultraviolet radiation source 53 are not shown for simplicity.

An inner dialysis catheter 41 may be made by a biocompatible material like; polyethene, Silicon or any other suitable material. A transparent outer tube 40 may be a flexible transparent (to an ultraviolet radiation) plastic tubing with a thickness of about 0.03 to 2 mm, preferably to be about 0.05 to about 1 mm or any suitable thickness. A catheter assembly 32 may be of any suitable size between 6 to 16 French circumferences, or any other suitable size and may be of different lengths as in standard dialysis catheter.

A catheter assembly 32 may have an exterior with generally round or any other shapes in cross section. An inner dialysis catheter may have an internal longitudinally extending lumens of D-shape, or circular, or any other shapes and may have a circular, or any other shapes in cross section.

A catheter assembly 32 may have at its distal end 32a, an end opening 43 (venous end opening as in standard hemodialysis catheter), an end opening 42 (arterial end opening as in standard hemodialysis catheter), and a different coil sensor 52. Also, a catheter assembly 32 may have at its proximal end, a Hub 45 that may attached with suture wings Assembly 44, which in turn may be connected to extension tubings 48 and 49, luer connectors 50 and 51 and may have clamps 46 and 47 as is standard in hemodialysis catheters. Extension Tubings 48 and 49 may fluidly connects catheter lumens 56 and 57 to a blood treatment unit or a hemofiltration machine (not shown for simplicity). Cable 36 with socket 34 to may connect a catheter assembly 32 to a device 31.

An ultraviolet radiation source comprises many rings assembles 54 of ultraviolet curved light emitting diode (LED) chips 54a. It must be pointed out that the intensity of an ultraviolet radiation (an ultraviolet output, as represented by arrows 55) must be such that the rays are strong enough to destroy microbes and to may transmit energy to the blood that empowers a strong biochemical response thereto, increasing stabilization of white blood cells, and increasing cell membrane permeability (which may enhance the body's ability to produce antibodies).

Figure 5:
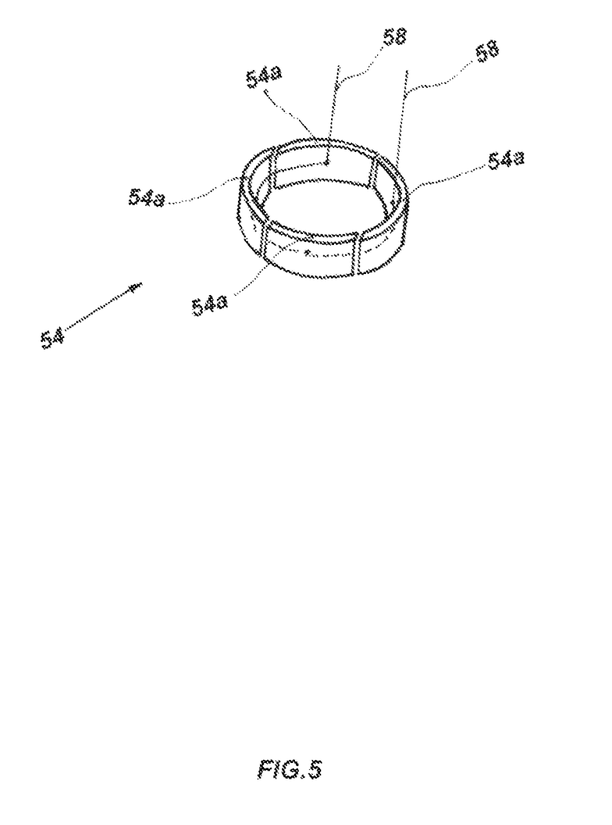
FIG. 5 is an enlarged view of one ring assembly of ultraviolet curved light emitting diode (LED) chips according to the present disclosure.

A ring assembly 54 of ultraviolet curved light emitting diode chips 54a may produce wavelengths range that may be between about 230 to 280 nm and preferably from 248 to 270 nm. An ultraviolet radiation source 53 may deliver ultraviolet output 55 to a blood in a dose ranging from about 1 mV/cm2 to about 20 mV/cm2 based on a blood flow rate and continuous or pulsed ultraviolet mode. Preferably dose may be about 3 to about 10 my/cm2 or any suitable dose. Ultraviolet curved light emitting diode chips 54a may have a higher energy, a concentrated power and a lower heat generation.

FIG. 4a illustrates an enlarged cross-sectional view of the catheter assembly 32 without stylet 34 taken along line 4a-4a of FIG. 4, wherein an inner dialysis catheter 41 which may have a D-shape with catheter lumens 56 and 57, a transparent outer tube 40 and ultraviolet curved light emitting diode chips 54a

FIG. 5 illustrates enlarged view of a ring assembly 54 of ultraviolet curved light emitting diode chips 54a and wires 58 to may power ultraviolet curved light emitting diode chips 54a. These wires 58 may be gold wires or any suitable wires.

Figure 6:
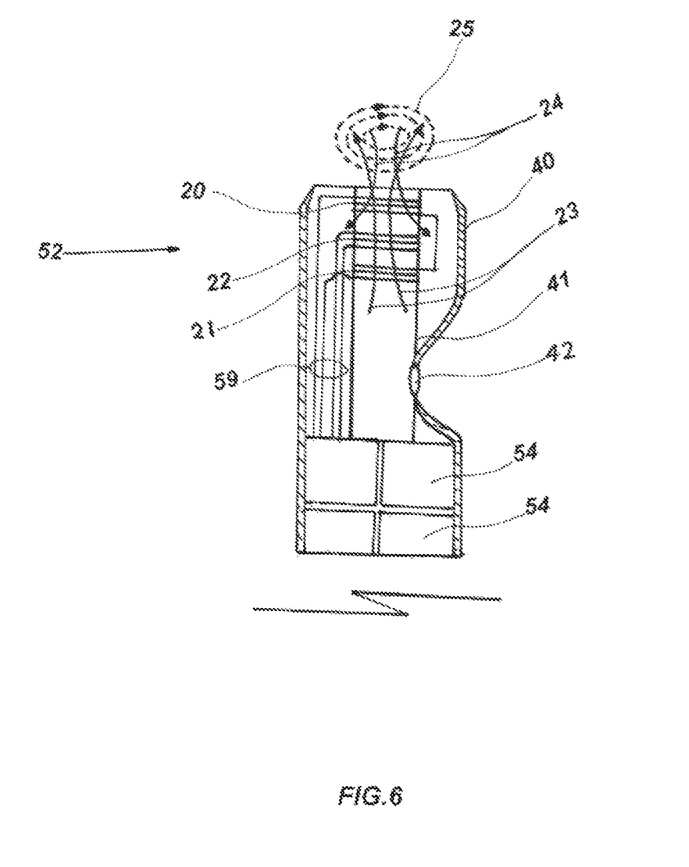
FIG. 6 is an enlarged view of a differential coil sensor located at the distal tip of catheter assembly according to the present disclosure.

FIG. 6 illustrates an enlarged view of a differential coil sensor 52 located at a distal tip 32a of a catheter assembly 32, wherein a transmitter coil 22 and two receiver coils 20 and 21. A transmitter coil 22 and two receiver coils 20 and 21 are formed by a conductive material like aluminum, copper, silver or the like and are wound on an external surface of an inner dialysis catheter 41. The windings of a transmitter coil 22 and two receiver coils 20 and 21 are extended on a cylindrical lateral surface of an external surface of an inner dialysis catheter 41. Also, a transmitter coil 22 and two receiver coils 20 and 21 are arranged axially one after the other and two receiver coils 20 and 21 are at the same distance from a transmitter coil 22 on oppositely lying sides of a transmitter coil 22.

After an activation of a differential coil sensor 52, a transmitter coil 22 receives an alternating current to generate a primary flux 23 to produce eddy currents 25 in the blood. Secondary flux 24 generated by eddy currents 25 is linked through differentially connected receiver coils 20 and 21. This caused a gradient voltage 26 (Vout) as in FIG. 2 which is directly proportional to a conductivity of the blood. The gradient voltage 26 is proceeded to an electronic circuit inside a device 31 (not shown for simplicity) to be displayed on a screen 67 as an actual conductivity measurement of the blood and a differential conductivity ΔC. Those skilled in the art will recognize that microbes are very acidic and when they are killed, acidic waste is created in the blood, which may be reflected on blood conductivity readings and on differential conductivity ΔC, to may enable the user to evaluate the treatment process during the operation. Still in FIG. 6, wherein a ring assembly 54 and differential coil sensor's wires 59.

Figure 7:
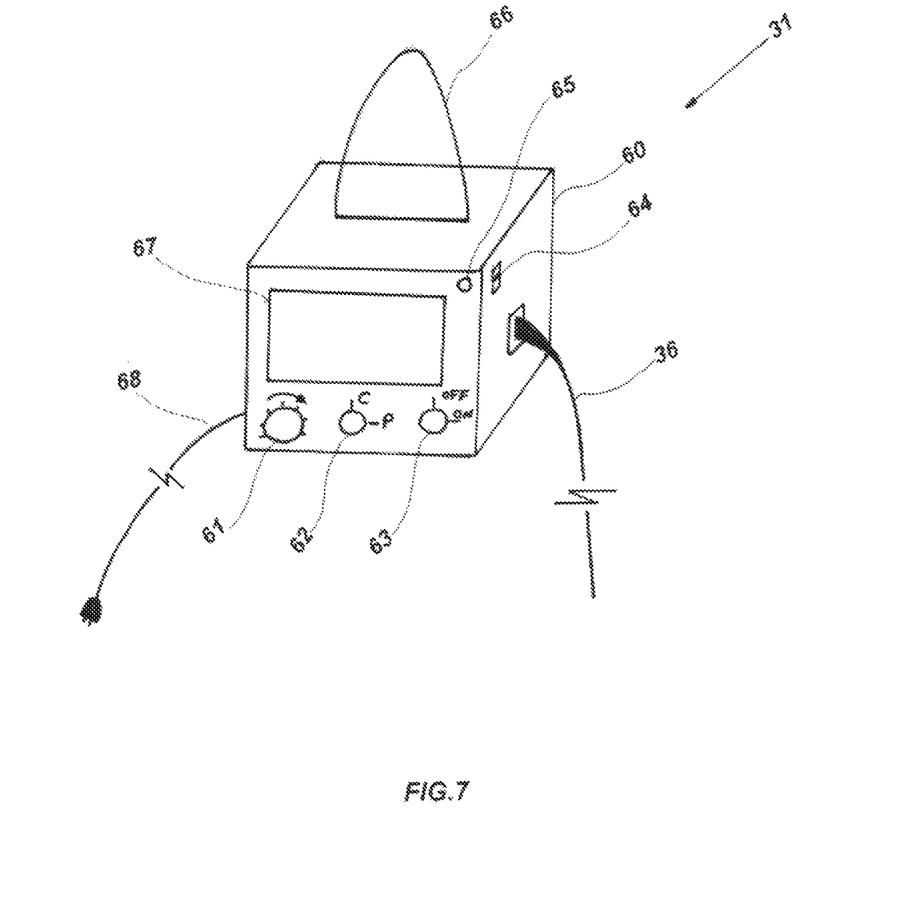
FIG. 7 is an enlarged view of the device that power, control and monitor an ultraviolet radiation as well as to monitor a blood conductivity according to the present disclosure.

FIG. 7 illustrates an enlarged view of a device 31 to may power, control and monitor an ultraviolet radiation as well as to may monitor a blood contactless conductivity wherein, a device housing 60, a power switch 64 to activate the device, an ultraviolet intensity setting button 61 to set up the required intensity, a continuous or pulsed selection switch 62 to select either continuous radiation mode or pulsed radiation mode, an ultraviolet ON/OFF switch 63 to activate ultraviolet radiation whenever it is required, an alarm LED (light emitting diode) 65 to be flushing with an auditable beep in case of an alarm, a belt 66 to hang a device 30 on an IV pole, a power cord 68 for a power supply, a cable 36 to connect a device 31 to a catheter assembly 32 and a screen 67. A screen 67 may be used to monitor an actual ultraviolet intensity based on an ultraviolet sensor reading (not shown for simplicity) and an ultraviolet setting as it sets up using an ultraviolet intensity button 61, as well as it may monitor a blood conductivity measurement and a differential conductivity ΔC.

In operation a catheter assembly 32 with an inner dialysis catheter 41, an ultraviolet radiation source 53 and a differential coil sensor 52 may be inserted in a femoral vein using a standard insertion technique and may connected to a device 31, to may irradiate the blood with an ultraviolet radiation to may destroy infectious microbes directly in the blood, to may transmit energy to the blood that empowers a strong biochemical response thereto, increasing stabilization of white blood cells, and increasing cell membrane permeability (which may enhance the body's ability to produce antibodies) and to may measure a blood contactless conductivity during the operation. Furthermore, it may destroy microbes indirectly (secondary radiations) at an initial point of infection without effecting the cells themselves. Destruction of microbes inside the cells by an ultraviolet radiation, may revert them into normal cells.

The treatment session may have a duration that may be from about 2 hours to about 4 hours or any suitable duration based on patient's condition. The treatment sessions may be repeated based on patient's vitality and condition until normal bodily functions are permitted without any further aid. In another implementation, The treatment session may be followed by a hemofiltration session using a portable hemofiltration machine to may help to infuse medication/s and to may help to remove circulating and endotoxins mediators from the blood by filtration as in this case a catheter assembly may be disconnected from a device 31 via a socket 34 and used as a standard dialysis catheter (no need to insert another catheter).

The invention claimed is:

1. A process, comprising two phases of operation:
   a phase one which is a blood irradiation session wherein,
      a catheter assembly comprising an inner dialysis catheter body, two end openings at its distal end, two extension tubes with luer connectors at its proximal end, an ultraviolet radiation source, and a differential coil sensor at the distal end is inserted in a vein;
   wherein the differential coil sensor comprises one transmitter coil arranged between two receiver coils;
   wherein the catheter assembly is connected to a device that powers, controls, and monitors the ultraviolet source and differential coil sensor with a cable;
   irradiating blood with ultraviolet radiation via said ultraviolet radiation source to destroy microbes until normal bodily functions are observed while measuring blood conductivity with the differential coil sensor to measure acidic waste created by destroyed microbes using the device;
   a second phase which is a hemofiltration session wherein, the catheter assembly is disconnected from the device and is connected to a hemofiltration machine to infuse medication/s and to remove circulating endotoxins from the blood by filtration.

2. The process of claim 1, wherein irradiating the blood with ultraviolet radiation directly destroys the microbes.

3. The process of claim 2, wherein irradiating the blood with ultraviolet radiation induces hemoglobin to continuously vibrate and emit secondary ultraviolet radiations that destroy microbes.

* * * * *